United States Patent [19]
Roch

[11] 3,933,035
[45] Jan. 20, 1976

[54] INSTALLATION FOR CONTINUOUS MEASUREMENT OF THE ELASTIC COEFFICIENT OF A TRAVELING STRIP, WIRE OR RIBBON

[75] Inventor: Roger Henri Roch, Lausanne, Switzerland

[73] Assignee: J. Bobst & Fils S.A., Switzerland

[22] Filed: Sept. 5, 1974

[21] Appl. No.: 503,295

[30] Foreign Application Priority Data
Sept. 19, 1973 Switzerland..................... 13482/73

[52] U.S. Cl. .............................................. 73/95.5
[51] Int. Cl.² ......................................... G01N 3/00
[58] Field of Search..................... 73/143, 144, 95.5

[56] References Cited
UNITED STATES PATENTS

| | | | |
|---|---|---|---|
| 1,851,895 | 3/1932 | Cornet | 73/95.5 |
| 2,634,607 | 4/1953 | Lawson | 73/95.5 |
| 3,274,824 | 9/1966 | Lawson et al. | 73/95.5 |
| 3,366,299 | 1/1968 | Rose, Jr. et al. | 73/95.5 X |

FOREIGN PATENTS OR APPLICATIONS
841,255  7/1960  United Kingdom.................. 73/95.5

Primary Examiner—Charles A. Ruehl
Attorney, Agent, or Firm—Hill, Gross, Simpson, Van Santen, Steadman, Chiara & Simpson

[57] ABSTRACT

Apparatus for the continuous measurement of the elastic coefficient of a traveling strip, wire or ribbon, is characterized in that it employs first and second means for driving the strip arranged one behind the other in the direction of motion of the strip. The second driving means drives the strip at a speed different from that of the first driving means and first and second tension measuring devices are disposed in front of the first and second driving means, respectively, and deliver respective quantities which are proportional to the tensions measured thereby. A comparator circuit is provided for determining the difference in the measured tensions, this difference being proportional to the elastic coefficient of the strip.

5 Claims, 3 Drawing Figures $(1-e^{-\frac{t}{\tau}})T_1$

INSTALLATION FOR CONTINUOUS MEASUREMENT OF THE ELASTIC COEFFICIENT OF A TRAVELING STRIP, WIRE OR RIBBON

BACKGROUND OF THE INVENTION

1. Field of the Invention

This invention relates to apparatus for continually measuring the elastic coefficient of a traveling strip, wire or ribbon.

2. Description of the Prior Art

Solutions for measuring the elastic coefficient of a strip which are based on the measurement of the difference in speed of the strip between two points at different tensions are known in the art. These systems do not, however, provide satisfactory results because a relatively small difference is being measured in comparison to the speeds of the strip at the points of measurement.

SUMMARY OF THE INVENTION

The primary object of the present invention is to provide a new and improved installation for the continuous measurement of the elastic coefficient of a traveling strip, wire or ribbon.

A more particular object of the invention is to provide a continuous measurement of the elastic coefficient of a traveling strip, wire or ribbon, which measurement is accurate.

The advantages of an installation of the type set forth herein, in particular, enables a solution of the problem of the introduction of a strip of paper or cardboard, taken from a reel, into a printer group, for example, by satisfying certain conditions which include the introduction of the material at a constant tension, the introduction of the material at a constant stretch to guarantee constant format at rest, and the introduction of the material at a constant stretch under predetermined tensioning to guarantee constant format at a given tension.

Although the invention is exemplified hereinbelow as applying to a traveling strip, the invention is not restricted to a particular width of the material or to a particular material. This structure will therefore be hereinafter referred to only as a strip in that there are many applicable cases in which continuous measurement of the elastic coefficient can provide valuable information. By way of example, it may be mentioned that quality control of a product manufactured in web form, whether paper, cardboard, plastic material, or metal may take advantage of the invention. Due to continuous measurement of the elastic coefficient it is possible to carry out a quality check in a continuous manner at the output of a machine which produces the strip. The value measured may be employed for ensuring automatic regulation of the producing machine.

According to the invention the installation is characterized in that it comprises a first means of driving the strip and a second means of driving the strip arranged behind the first driving means in the direction of motion of the strip. The second driving means drives the strip at a speed that is different from that provided by the first driving means. A first device for measuring the tension in the strip is located on the upstream side of the first driving means and is operable to deliver a first quantity which is proportional to the tension measured thereby. A second device for measuring the tension in the strip is located upstream of the second driving means and is operable to deliver a second quantity which is proportional to the tension measured thereby. A comparator circuit is connected to receive the two quantites measured by the first and second tensioning measuring devices and operates to provide a quantity which is proportional to the difference in the tensions measured, this difference being proportional to the elastic coefficient of the strip.

In order to improve the quality of the measurement under dynamic operation, a correction factor may be introduced to take into account the time constant affecting propagation of a variation in the tension of the strip from the first tension measuring device to the second tension measuring device. This time constant is due to the effect upon the strip of the two driving means.

BRIEF DESCRIPTION OF THE DRAWINGS

Other objects, features and advantages of the invention, its organization, construction and operation will be best understood from the following detailed description taken in conjunction with the accompanying drawings, on which.

DESCRIPTION OF THE PREFERRED EMBODIMENT

Figure 1:
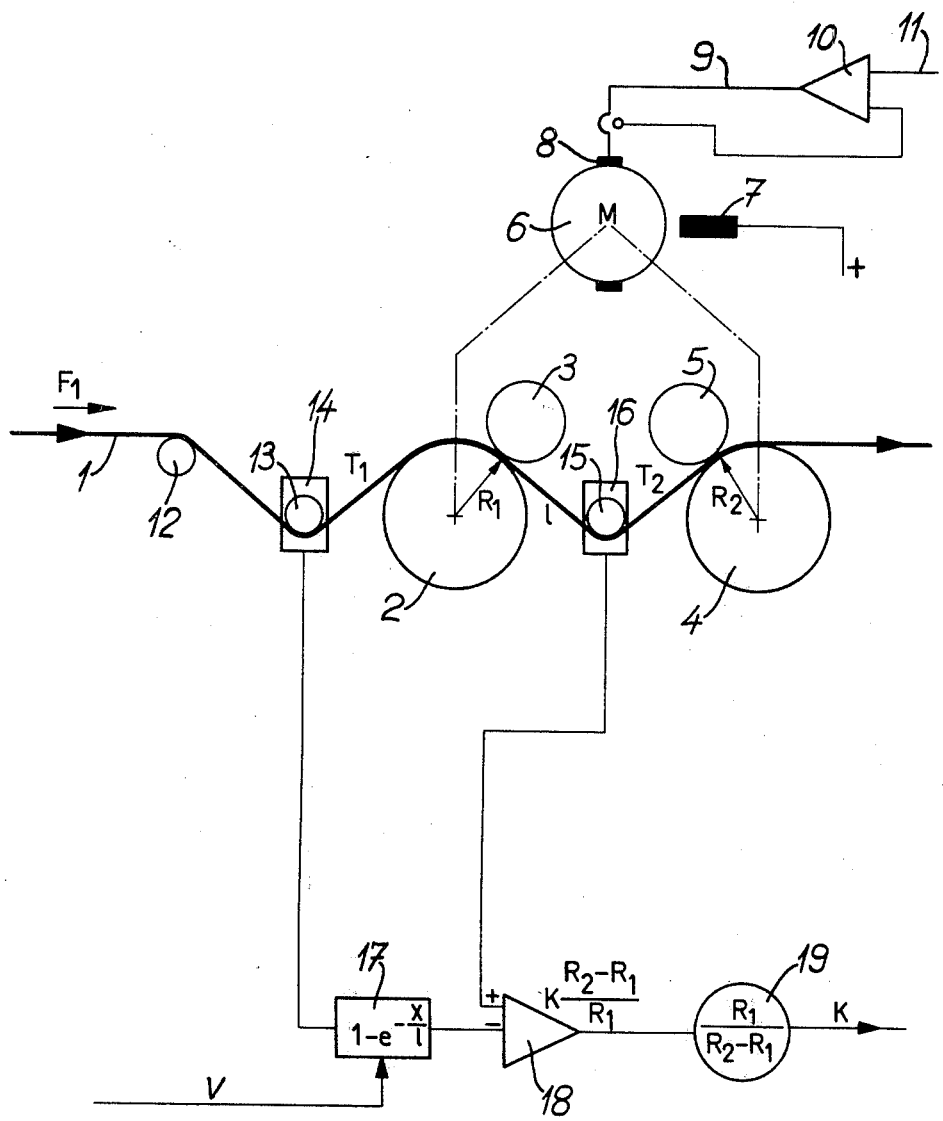
FIG. 1 is a schematic representation of an installation constructed in accordance with the principles of the invention.

Referring to FIG. 1 a strip 1, for example a strip of paper, from a reel and unwound in the direction of the arrow $F_1$ is driven by a mechanical assembly comprising a first draw roll 2 having a radius $R_1$ cooperating with a pressure roll 3 and a second draw roll 4 having a radius $R_2$ cooperating with a pressure roll 5. The draw rolls 2 and 4 are driven at the same angular velocity by a motor 6. This motor is a d.c. motor having a constant field excitation structure 7 which is well known in the art. The motor 6 includes an armature 8 which is fed by a static feed comprising a loop 9 for controlling the armature current. The loop 9 is closed through an operational amplifier 10 which has an input 11 which may be energized with a value corresponding to the desired driving torque.

The strip 1 additionally passes over a fixed axis pulley 12, under a pulley 13 carried by a first strip tension measuring device 14 located in front of the draw roll 2 and under a third pulley 15 carried on a second tension measuring device 16 located in front of the second draw roll 4. The tension measuring devices 14 and 16 are well known per se and commonly employed for obtaining an electrical quantity which is proportional to the mechanical tension exerted on a strip.

The arrangement further comprises a device 17 which introduces a time constant in accordance with the function $1 - e^{-x/t}$ to which is applied, on the one hand, the electrical quantity delivered by the tension measuring device 14, and, on the other hand, an electrical quantity which is proportional to the velocity of motion $v$ of the strip. A circuit 18 comprising an operational amplifier is connected to receive the respective electrical quantities at its (+) and (−) inputs and is operable to deliver a signal which is proportional to the difference between these electrical quantities. The operational amplifier 18 feeds a divider circuit 19 which provides an electrical quantity which is proportional to the elastic coefficient of the strip 1.

The radius $R_2$ of the draw roll 4 is slightly larger than the radius $R_1$ of the draw roll 2, in the order of 1%. Inasmuch as the angular velocities of the draw rolls 2 and 4 are the same, this difference in radius imposes an increase in the velocity of the strip of 1% between the draw rolls 2 and 4, that is to say a predetermined increase in the specific stretch of the strip which is equal to $R_2 - R_1/R_1$.

The elastic coefficient K is equal to the ratio "increase in tension/increase in stretch" one obtains in stationary operation $$K = \frac{T_2 - T_1}{R_2 - R_1} \cdot R_1,$$

$T_1$ and $T_2$ being the mechanical tensions measured by the respective tension measuring devices 14 and 16.

In dynamic operation it is advisable to take into consideration the fact that a variation in the strip tension $T_1$ is not instantaneously reflected in the tension $T_2$, but is delayed by a "time constant" due to the two pairs of draw-pressure rolls 2, 3 and 4, 5.

This time constant is equal to the length of the strip 1 located between the two draw rolls and a disturbance $\Delta T_1$ is transmitted in accordance with the relationship
$$\Delta T_2 (T_1) = (1 - e^{-x/l}) \cdot \Delta T_1$$

Therefore, in order to make a valid comparison between the two sets of information proceeding from the tension measuring devices 14 and 16, it is advisable to permit the first measurement to electronically undergo the same "attenuation" function as the variations in the tension $T_1$ undergo before arriving at the level of the tension $T_2$.

With the introduction of this correction factor, the elastic coefficient under dynamic operation becomes $$K = \frac{T_2 - T_1(1 - e^{-x/l})}{R_2 - R_1} \cdot R_1.$$

By introducing this time constant there is then obtained a continuous and accurate measurement of the elastic coefficient K whatever the variations in the tension $T_1$. The difficulty lies in going from the quantity "time" to the quantity "length". It has, however, been possible to achieve this transformation in a relatively simple manner.

If the velocity of the strip 1 is designated $v$ and the path covered by the strip during the time $t$ is designated $x$, one obtains the relationships
$$x = v.t$$
and
$$1 - e^{-x/l} = 1 - e^{-vt/l} = 1 - e^{-t/\tau}$$

Consequently, it is necessary to consider by analogy a time constant which is a function of the velocity by producing the relationship
$$\tau(v) = l/v$$

Figure 2:
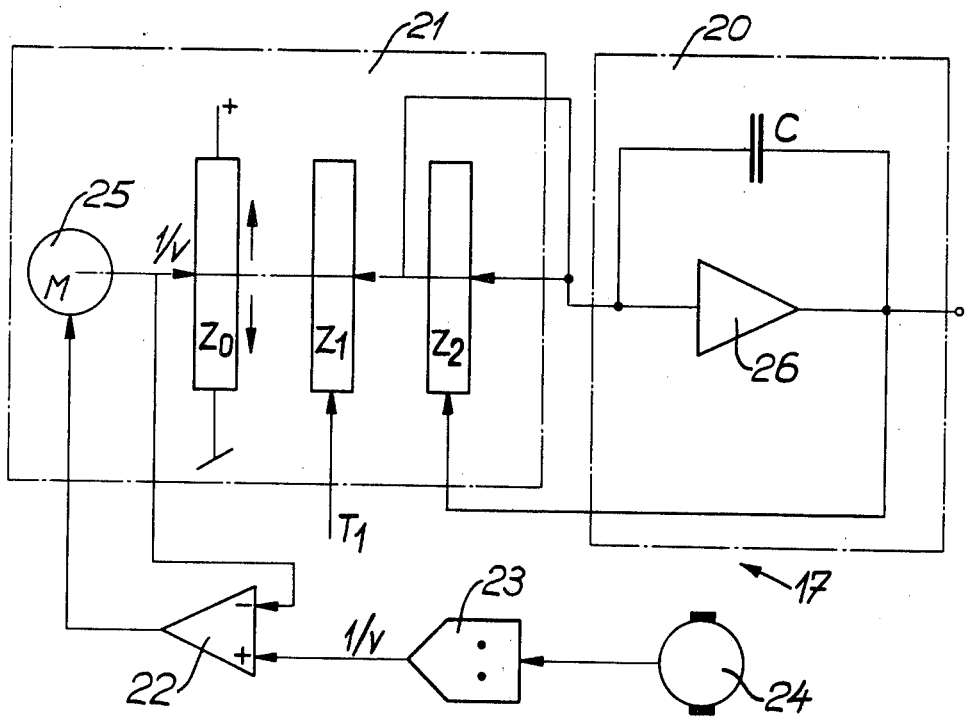
FIG. 2 is a schematic representation of a collection device which may be employed in practicing the invention.

The circuit 17 accurately produces the function $1 - e^{-x/l}$ as a function of the velocity $v$ of the strip measured by means of a tachometer. The circuit 18 delivers an electrical quantity proportional to
$$T_2 - T_1 (1 - e^{-x/l})$$
and the circuit 19 divides this quantity by a factor proportional to $R_2 - R_1/R_1$ The function $1 - e^{-vt/l}$ is produced by means of the device represented in FIGS. 2 and 3. This device comprises an integrator 20, an accurate servo-potentiometer 21, an operational amplifier 22, and an electronic divider 23 which ensures mathematical inversion of a quantity proportional to the velocity $v$ delivered by a tachometer 24 comprising a tachometric generator. The various elements of this circuit are per se well known and readily available on the market.

The circuits 22 and 23 may advantageously be constructed as integrated circuits. The servo-potentiometer 21 comprises a servomotor 25 which simultaneously drives the cursors of three variable resistors $Z_0$, $Z_1$ and $Z_2$. The variable resistor $Z_0$ is connected between a positive voltage and ground and has its cursor connected to the (−) input of the operational amplifier 22. At the other input (+) of the operational amplifier 22 a voltage is applied which is proportional to $1/v$ received from the output of the electronic divider circuit 23.

Figure 3:
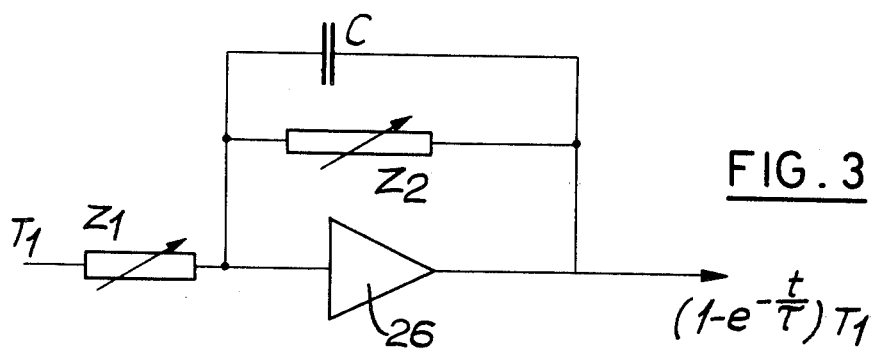
FIG. 3 is a schematic circuit diagram of a portion of the correction device for introducing the analog function $1 - e^{-x/t}$.

The resistors $Z_1$ and $Z_2$ are connected respectively in series and in parallel with the operational amplifier 26 of the integrator 20, as is made more readily apparent in the electrical schematic circuit of FIG. 3. A capacitor C is connected in parallel with the resistor $Z_2$. The electrical quantity which is proportional to the mechanical tension $T_1$ is applied to the other terminal of the variable resistor $Z_1$. This circuit reproduces the function
$$T_1 (1 - e^{-t/\tau}) \text{ or } \tau = Z_2 C$$

As the time constant $\tau$ is proportional to the resistance $Z_2$, and as the resistance $Z_2$ varies as a function of $1/v$, the function required is correctly obtained. The aforedescribed structure may be modified such that the quantities which are proportional to the tensions and the quantities which are calculated may be obtained or calculated, respectively, by means other than electrical. For example, mechanical, hydraulic, pneumatic or hydropneumatic means, in particular fluidic circuits, may be employed in practicing the invention.

Although I have described my invention by reference to a particular embodiment thereof, many other changes and modifications of the invention may become apparent to those skilled in the art without departing from the spirit and scope of the invention. I therefore intend to include within the patent warranted hereon all such changes and modifications as may reasonably and properly be included within the scope of my contribution to the art.

I claim:

1. Apparatus for continuously measuring the elastic coefficient of a moving strip, comprising:

first and second drive means for driving the strip, said second drive means arranged behind said first drive means with respect to the direction of motion of the strip and operable to drive the strip at a speed different from that provided by said first drive means;

first and second tension measuring devices respectively positioned in front of said first and second drive means and operable to continuously provide respective first and second quantities which are proportional to the strip tensions measured at those positions; and comparison means connected to said first and second tension measuring devices and responsive to said first and second quantities to continuously provide a third quantity which is proportional to the difference in the measured tensions, which is proportional to the elastic coefficient of the strip.

2. Apparatus according to claim 1, wherein:

said first and second drive means each comprises a draw roll and a pressure roll to receive the strip therebetween, and means rotating said draw rolls at the same angular velocity, and wherein the radius of said first draw roll is smaller than the radius of said second draw roll.

3. Apparatus according to claim 1, and further comprising:

delay means connected between said first tension measuring device and said comparison means, said delay means having a time constant which is a function of the speed of the strip and the length of the strip between said first and second drive means.

4. Apparatus for continuously measuring the elastic coefficient of a moving strip, comprising:

first and second drive means for driving the strip, said second drive means arranged behind said first drive means with respect to the direction of motion of the strip and operable to drive the strip at a speed different from that provided by said first drive means;

first and second tension measuring devices respectively positioned in front of said first and second drive means and operable to provide respective first and second quantities which are proportional to the strip tensions measured at those positions;

comparison means connected to said first and second tension measuring devices and responsive to said first and second quantities to provide a third quantity which is proportional to the difference in the measured tensions, which is proportional to the elastic coefficient of the strip;

delay means connected between said first tension measuring device and said comparison means, said delay means having a time constant which is a function of the speed of the strip and the length of the strip between said first and second drive means; and speed indicating means for providing a fourth quantity which is proportional to the speed of the strip, and wherein said delay means includes analog means connected to said speed indicating means and responsive to said fourth quantity to produce the time constant in accordance with the function $1 - e^{-x/t}$, where x is the path covered by the moving strip during a time t and l is the length of the strip between the first and second drive means.

5. Apparatus for continuously measuring the elastic coefficient of a moving strip, comprising:

first and second drive means for driving the strip, said second drive means arranged behind said first drive means with respect to the direction of motion of the strip and operable to drive the strip at a speed different from that provided by said first drive means;

first and second tension measuring devices respectively positioned in front of said first and second drive means and operable to provide respective first and second quantities which are proportional to the strip tensions measured at those positions;

comparison means connected to said first and second tension measuring devices and responsive to said first and second quantities to provide a third quantity which is proportional to the difference in the measured tensions, which is proportional to the elastic coefficient of the strip;

delay means connected between said first tension measuring device and said comparison means, said delay means having a time constant which is a function of the speed of the strip and the length of the strip between said first and second drive means; and speed indicating means for providing a fourth quantity which is proportional to the speed of the strip;

and wherein said delay means comprises;

a divider circuit connected to said speed indicating means to invert said fourth quantity, a servo-potentiometer including a servomotor and a plurality of variable resistors mechanically coupled to said servomotor, a first operational amplifier having a first input connected to said divider circuit, a second input connected to one of said variable resistors, and an output connected to operate said servomotor, and an integrator circuit including a second operational amplifier connected in parallel with a second of said variable resistors, said third variable resistor connected to said second operational amplifier and connected to receive said first quantity.

* * * * *